(12) United States Patent
Sauer

(10) Patent No.: US 11,812,947 B2
(45) Date of Patent: Nov. 14, 2023

(54) APPARATUS FOR SUTURE MANAGEMENT AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 286 days.

(21) Appl. No.: 17/388,167

(22) Filed: Jul. 29, 2021

(65) Prior Publication Data

US 2021/0353285 A1 Nov. 18, 2021

Related U.S. Application Data

(63) Continuation of application No. 16/268,112, filed on Feb. 5, 2019, now Pat. No. 11,123,063.

(60) Provisional application No. 62/626,181, filed on Feb. 5, 2018.

(51) Int. Cl.
| | | |
|---|---|---|
| A61B 17/06 | (2006.01) | |
| A61B 17/04 | (2006.01) | |
| A61B 17/02 | (2006.01) | |
| A61B 17/00 | (2006.01) | |

(52) U.S. Cl.
CPC .... *A61B 17/06061* (2013.01); *A61B 17/0469* (2013.01); *A61B 17/0218* (2013.01); *A61B 2017/00477* (2013.01)

(58) Field of Classification Search
CPC ............ A61B 17/0206; A61B 17/0218; A61B 17/0469; A61B 17/06061; A61B 2017/00243; A61B 2017/00477; A61B 2017/0406; A61B 2017/0409; A61B 2017/0417; A61B 2017/0464; A61B 90/92
See application file for complete search history.

(56) References Cited

U.S. PATENT DOCUMENTS

| | | | |
|---|---|---|---|
| 4,492,229 A | * | 1/1985 | Grunwald ........ A61B 17/06061 600/232 |
| 7,276,024 B1 | | 10/2007 | Royse |
| 7,338,504 B2 | | 3/2008 | Vidal |
| 8,162,952 B2 | | 4/2012 | Cohen |
| 2009/0005794 A1 | | 1/2009 | Lowry |
| 2010/0010475 A1 | | 1/2010 | Teirstein et al. |

(Continued)

FOREIGN PATENT DOCUMENTS

WO WO2015189100 12/2015

OTHER PUBLICATIONS

Product Literature; Tevdek Polydek 11.18 teleflex Gabbay-Frater, Suture Guide.

(Continued)

*Primary Examiner* — Mohamed G Gabr

(74) *Attorney, Agent, or Firm* — Michael E. Coyne

(57) ABSTRACT

A rack and an apparatus for suture management are disclosed. The apparatus for suture management includes one or more racks, each rack including a plurality of cassette locations, each cassette location having an inside suture holder, an outside suture holder, and a cassette receiver. The apparatus for suture management also includes a plurality of suture grooves. The apparatus for suture management further includes a plurality of rack connection points. The apparatus for suture management also includes an attachment feature which may accept another surgical tool or mounting adapter.

20 Claims, 21 Drawing Sheets

(56) References Cited

U.S. PATENT DOCUMENTS

2010/0191261 A1* 7/2010 Carter .............. A61B 17/06061
606/150

OTHER PUBLICATIONS

Video; Jan. 11, 2018; LSI Solutions; RAM AVR Knight product video, Link: https://www.youtube.com/watch?v=cWEXPzc5byg.
Office Action; dated Jun. 22, 2021, Yabe, Shintaro, Office Action from Japan Application No. 2020-541406.
Foreign Office Action; dated Jun. 22, 2021; Yabe, Shintaro; Office Action from JP2020541406.
Web Page; Jan. 24, 2018; LSI Solutions, Inc. Youtube Video: RAM Ring, https://www.youtube.com/watch?v=nlRL52PpM-E.

* cited by examiner

APPARATUS FOR SUTURE MANAGEMENT AND METHODS THEREOF

CROSS-REFERENCE TO RELATED APPLICATIONS

This patent application is a continuation of U.S. patent application Ser. No. 16/268,112, filed on Feb. 5, 2019 and entitled "APPARATUS FOR SUTURE MANAGEMENT AND METHODS THEREOF," which claims priority to U.S. Provisional Patent Application No. 62/626,181, filed Feb. 5, 2018 and entitled "APPARATUS FOR SUTURE MANAGEMENT AND METHODS THEREOF," each of which is incorporated by reference herein in its entirety.

FIELD

The claimed invention relates to surgical devices, and more specifically to devices used in the management of suture for minimally invasive surgical procedures.

BACKGROUND

Modern advances in minimally invasive cardiac surgery have enabled surgeons to perform surgical procedures which extend patient lives and improve patient quality of life while reducing post-operative pain, hospital stays, and post-operative limitations. Among such minimally invasive procedures, aortic valve replacement is one of the more challenging procedures. In addition to the specialized medical knowledge and surgical skills needed to complete such a procedure, surgeons and their medical staff must also be very adept at suture management. It is desirable to have improved apparatuses which help surgical staff with suture management. It would also be desirable to have improved apparatuses for suture management which interact efficiently with modern minimally invasive surgical tools.

SUMMARY

A rack for suture management is disclosed. The rack for suture management includes a plurality of cassette locations, each cassette location having an inside suture holder, an outside suture holder, and a cassette receiver. The rack for suture management also includes a plurality of suture grooves. The rack for suture management further includes a plurality of rack connection points. The rack for suture management also includes an attachment feature.

An apparatus for suture management is also disclosed. The apparatus for suture management may further include a plurality of racks, each rack including a plurality of cassette locations, each cassette location having an inside suture holder, an outside suture holder, one or more inside holding slots, one or more outside holding slots, and a cassette receiver. The apparatus for suture management also includes a plurality of suture grooves. The apparatus for suture management also includes a plurality of rack connection points. The apparatus also includes one or more soft inserts. The apparatus for suture management also includes at least one stabilizing foot and an attachment feature.

DETAILED DESCRIPTION

Figure 1A:
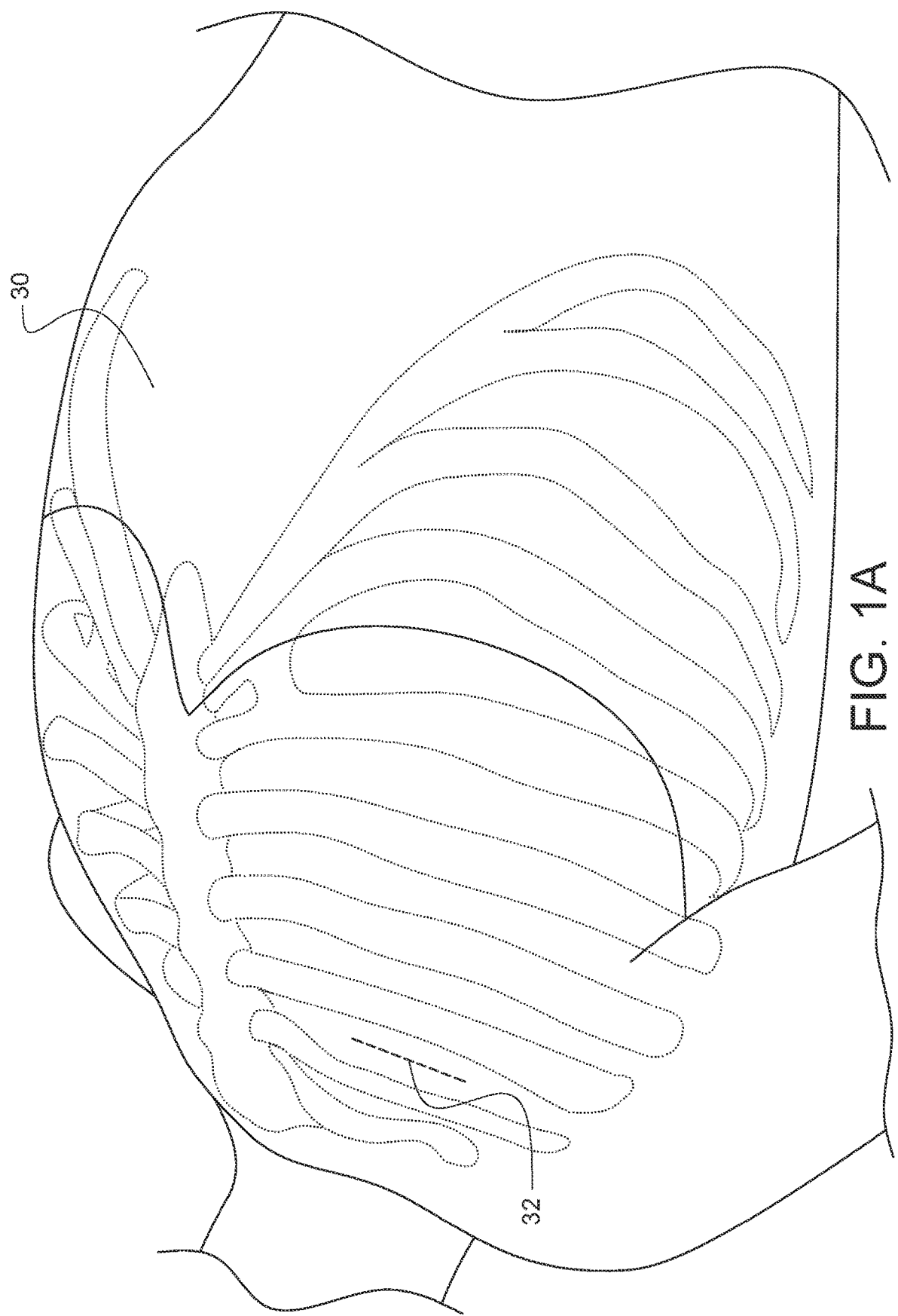
FIGS. 1A-1G are perspective views of a patient undergoing a portion of a minimally invasive cardiac surgical procedure.
Figure 1B:

FIGS. 1A-1G are perspective views of a patient undergoing a portion of a minimally invasive cardiac surgical procedure. FIG. 1A illustrates a portion of a possible surgical scenario. A patient's chest 30 is exposed, and an incision line 32 is marked on the patient's skin in the right second intercostal space (between the right second and third ribs). In an actual surgery, much of the area around the intended incision would be draped off, but for clarity, no such draping is shown in the illustrations herein. As illustrated in FIG. 1B, an incision 34 may be made through the skin and muscle tissue in the second intercostal space in order to expose the thoracic cavity 36.

Figure 1C:
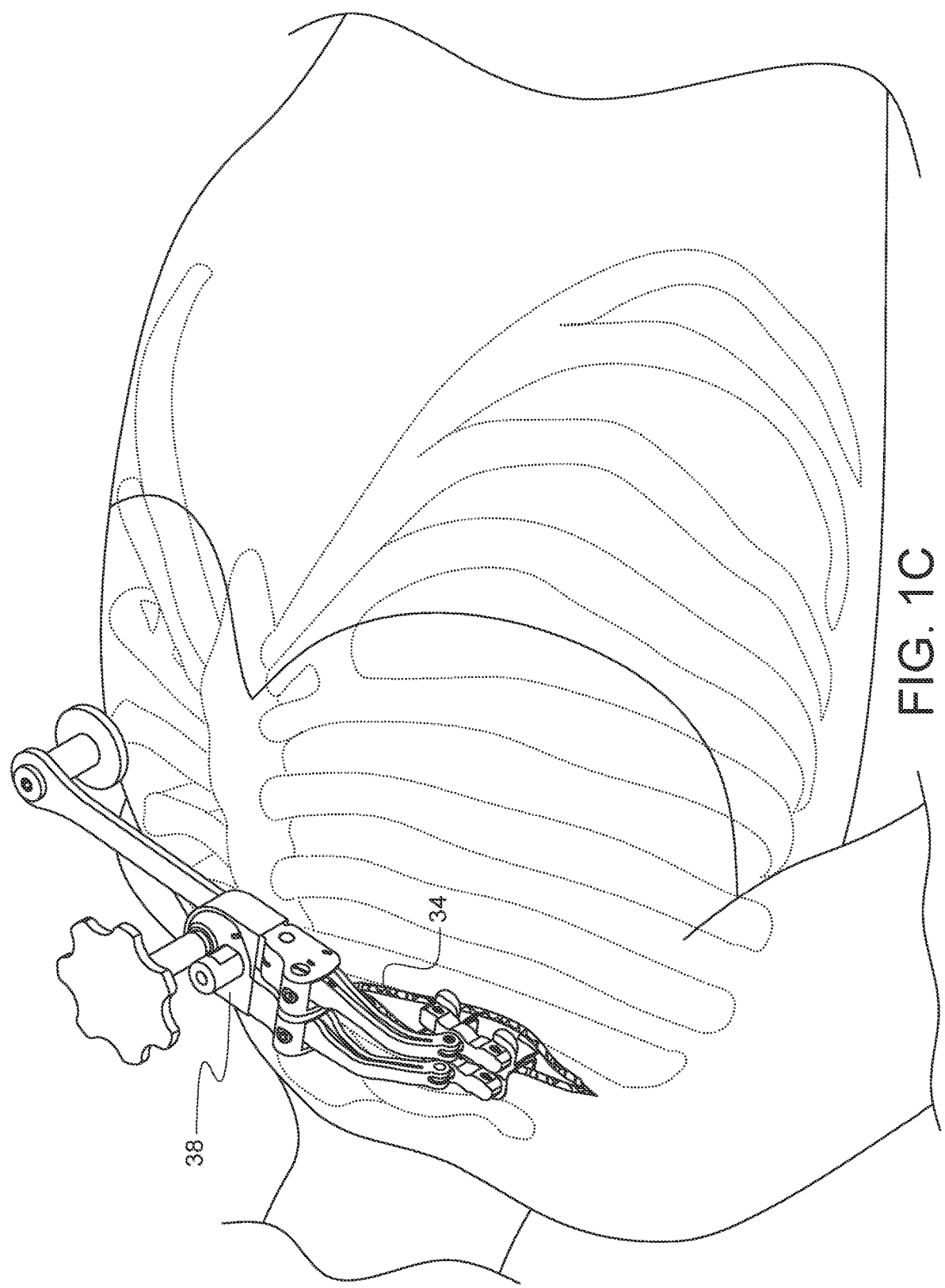
Figure 1D:
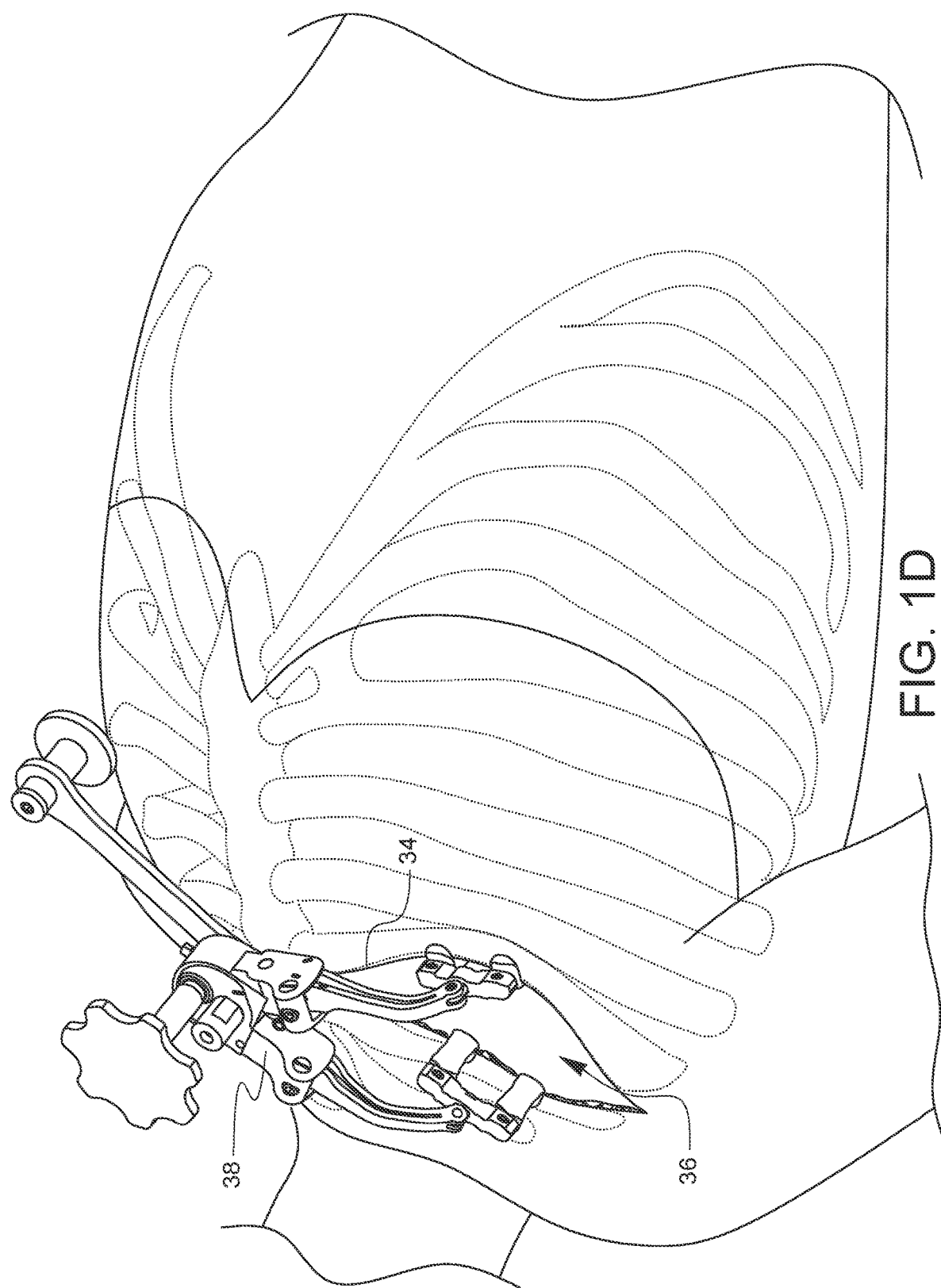
Figure 1E:
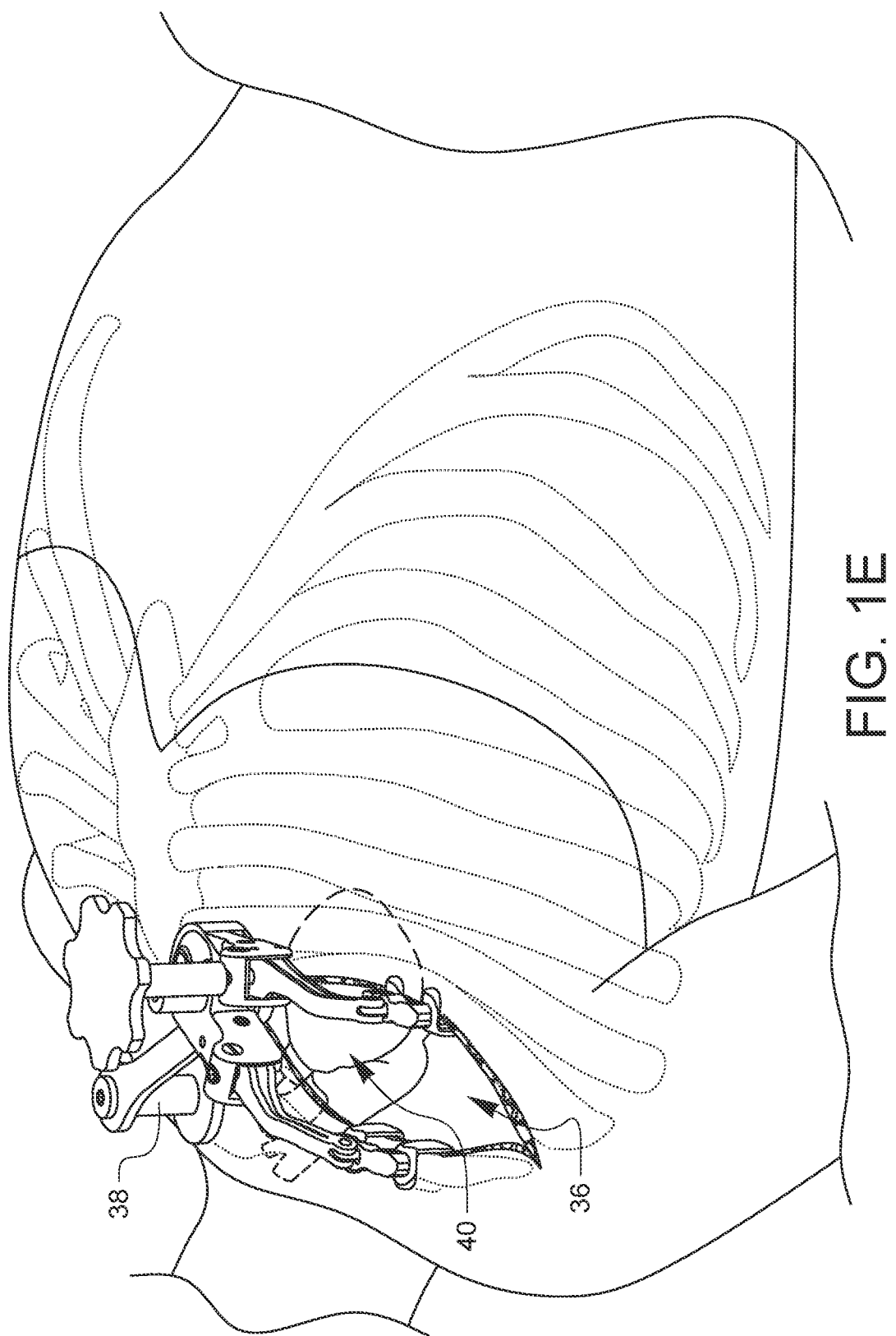

FIG. 1C illustrates the arms of a surgical retractor 38 being positioned within the incision 34 to engage the patient's ribs on either side of the incision 34. A wide variety of retractors may be used by surgeons, and the illustrated retractor 38 is just one example. The purpose of the retractor 38 is to spread the ribs, for example, as shown in FIGS. 1D and 1E, in order to provide more access to the thoracic cavity 36 and heart 40, enabling the necessary minimally invasive surgical instruments and any prostheses which might be needed to be placed into the thoracic cavity. Such minimally invasive surgical approaches are highly preferable to full or even partial sternotomies which are highly invasive, cause great pain, and result in very long hospital stays and patient recovery times.

Figure 1F:
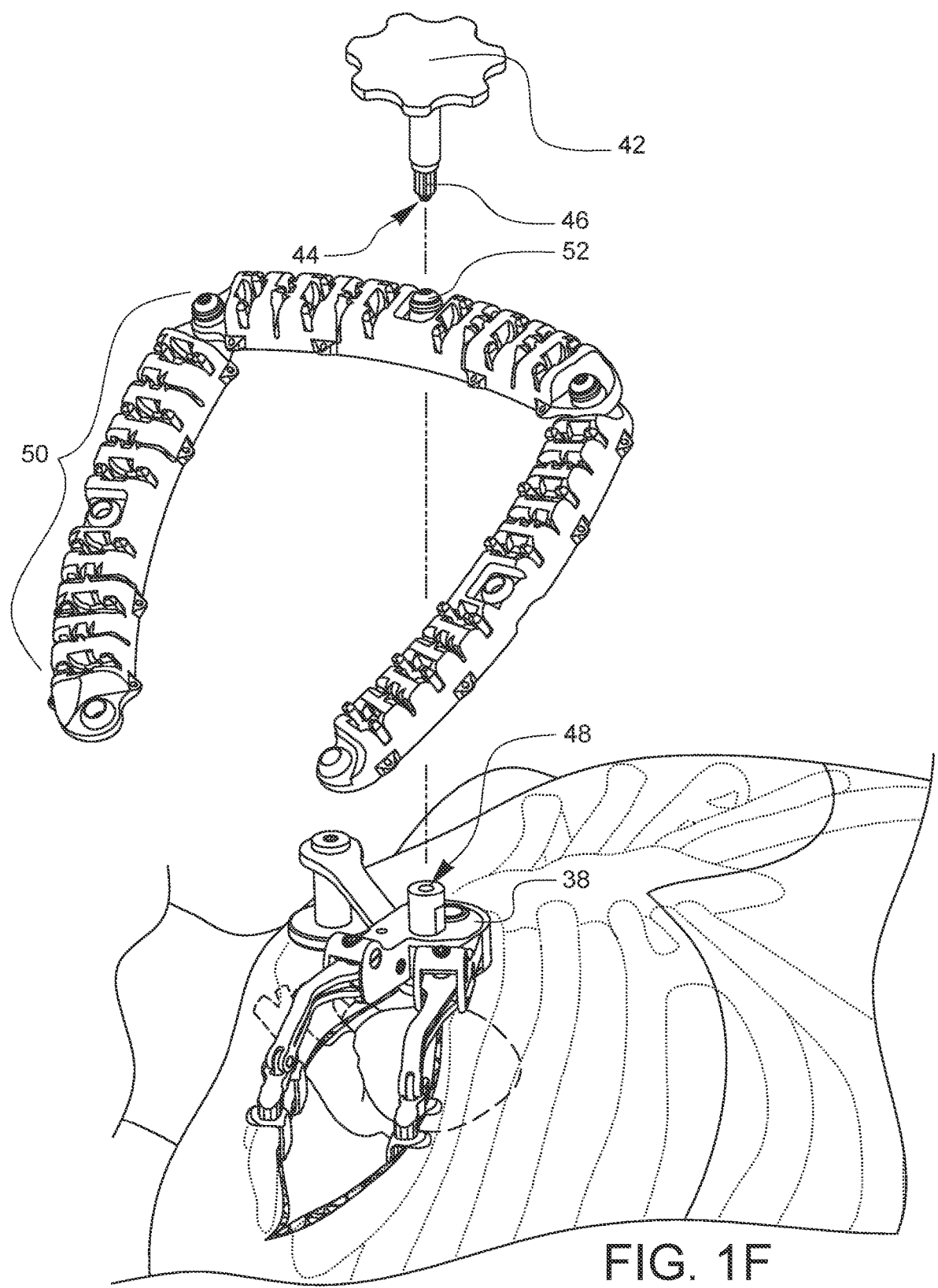

Referring to FIG. 1F, the illustrated retractor 38 has a knob 42 which is removable. For this type of retractor 38, the knob 42 has a key 44 and a gear 46 which are configured to be used to adjust the spread and height of the arms of the retractor 38. Regardless of whether or not the retractor 38 has such a removable control knob 42, the retractor 38 may have an accessory attachment point 48. With the knob 42 out of the way, an apparatus for suture management 50 may be coupled to the accessory attachment point 48 of the retractor 38. In FIG. 1F, the top of an attachment feature 52, in this example, a bolt 52, can be seen. The attachment feature 52 of the apparatus for suture management 50 is aligned with the accessory attachment point 48, which, in this example, is a tapped slot having threads which correspond to the threads of bolt 52.

Figure 1G:
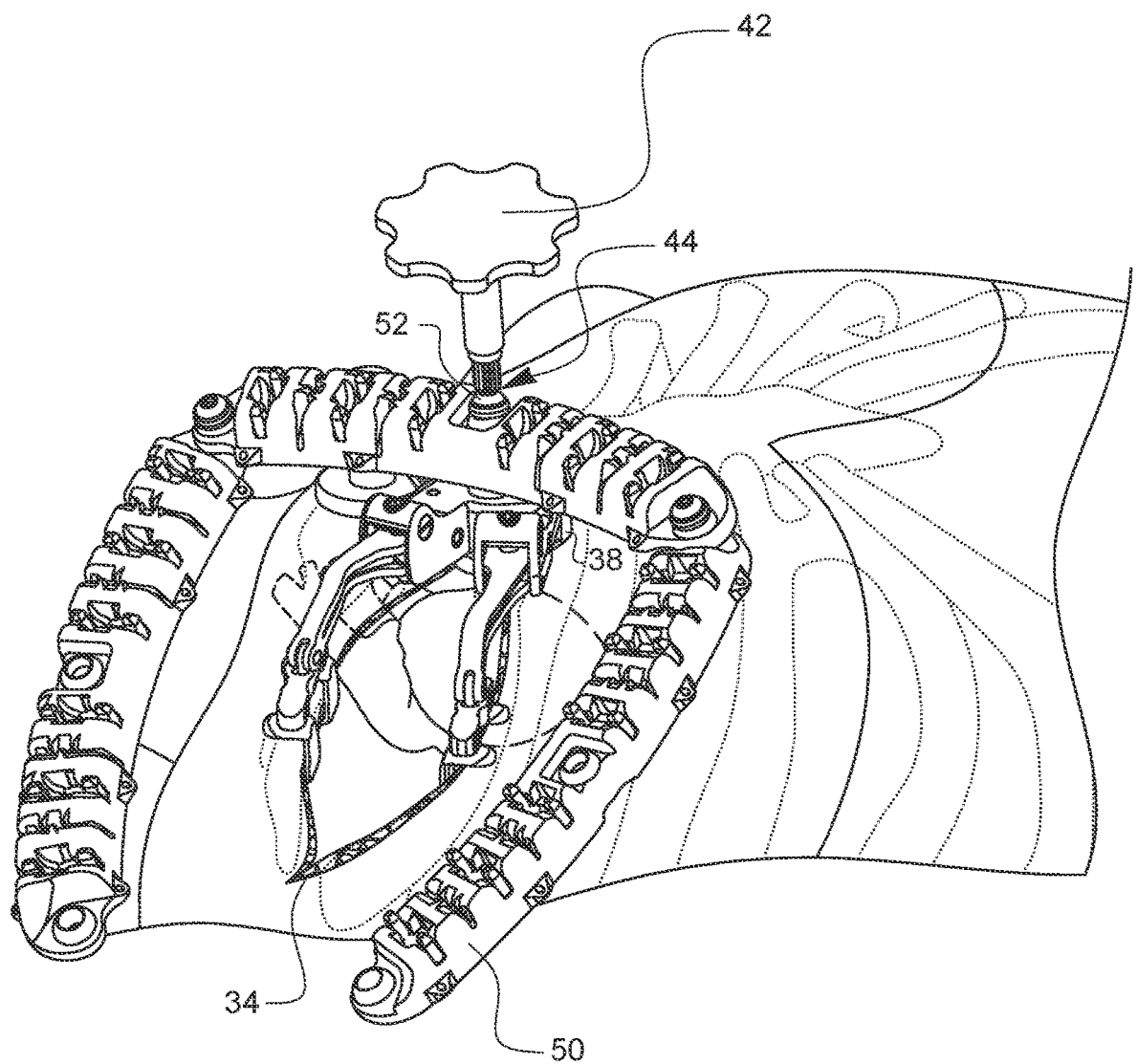

As illustrated in FIG. 1G, the apparatus for suture management 50 is coupled to the retractor 38 by tightening the bolt 52 into the accessory attachment point 48 (not visible in this view). While any suitable tool may be used to tighten the bolt 52, the attachment feature 52 may be configured to accept a readily available surgical tool, such as, but not limited to a control knob 42 from the rib retractor 38. In the example of FIG. 1G, the attachment feature 52 can be turned by the key 44 on the end of the knob 42 from the retractor 38. The apparatus for suture management 50 may be positioned around the incision 34 as desired, and then locked into place as the attachment feature 52 is secured. The attachment of the apparatus for suture management 50 need not be restricted to attachment to the retractor 38, as other bracing or surgical equipment holders may be employed for securing or mounting the apparatus for suture management 50 in a suitable location during a minimally invasive surgical procedure. Mounting or securing the apparatus for suture management 50 to a surgical equipment holder may optionally require an adapter. Various surgical equipment holders including, but not limited to, table mounts, supports, or articulating arm assemblies are known and described in the art.

Figure 2A:
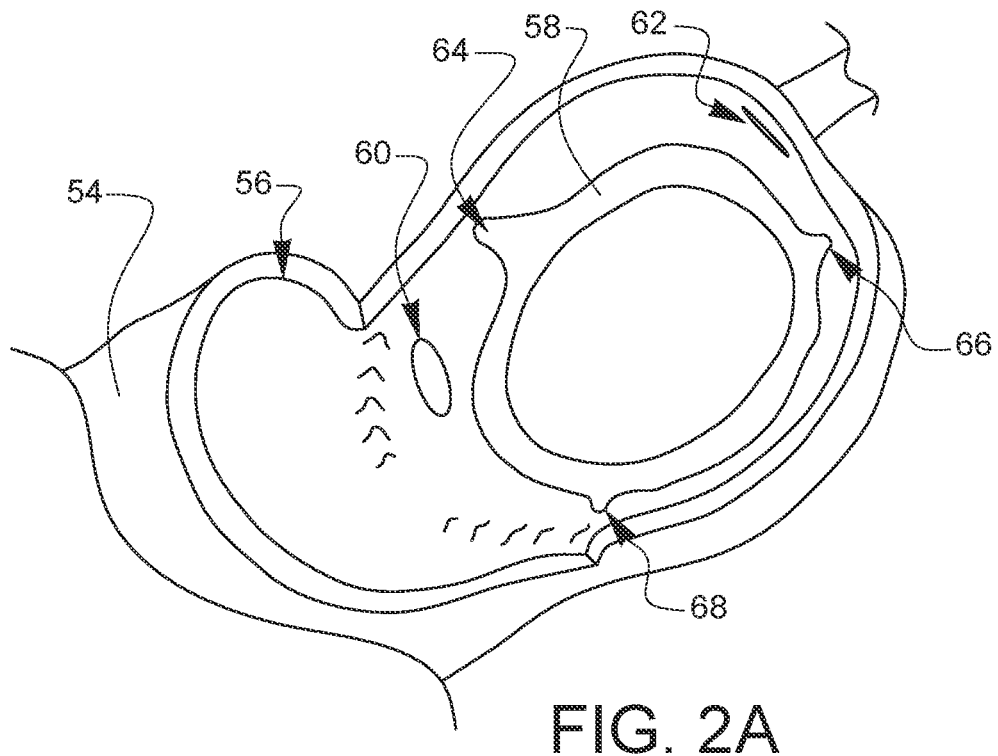
FIGS. 2A-2K are schematic views of several steps in a minimally invasive aortic valve replacement surgical procedure.

FIGS. 2A-2K schematically illustrate one example of several steps in a minimally invasive aortic valve replacement surgical procedure in order to provide an appreciation for why suture management can be so important. FIG. 2A illustrates an aorta 54 in which an aortotomy 56 has been made. The aortotomy 56 provides access to the aortic root 58 where the leaflets of the aortic valve meet the aorta 54. In FIG. 2A, diseased leaflets have already been dissected from the aortic root 58. Also visible is the left coronary sinus 60 and the right coronary sinus 62. Further visible is the left-right commissure 64, the right-non-coronary commissure 66, and the non-coronary-left commissure 68 of the aortic root 58. In order to keep the aortotomy 56 open so that all of these anatomical structures are visible and accessible, several stay sutures are typically placed in the aorta 54 near the edges of the aortotomy 56 in order to pull the aorta 54 out of the way. The stay sutures are not illustrated in this view, but they are merely to demonstrate that many sutures are needed for this type of procedure. Also, keep in mind that for every suture placed in tissue, there are two suture ends to manage, keep organized, and keep untangled.

Figure 2B:
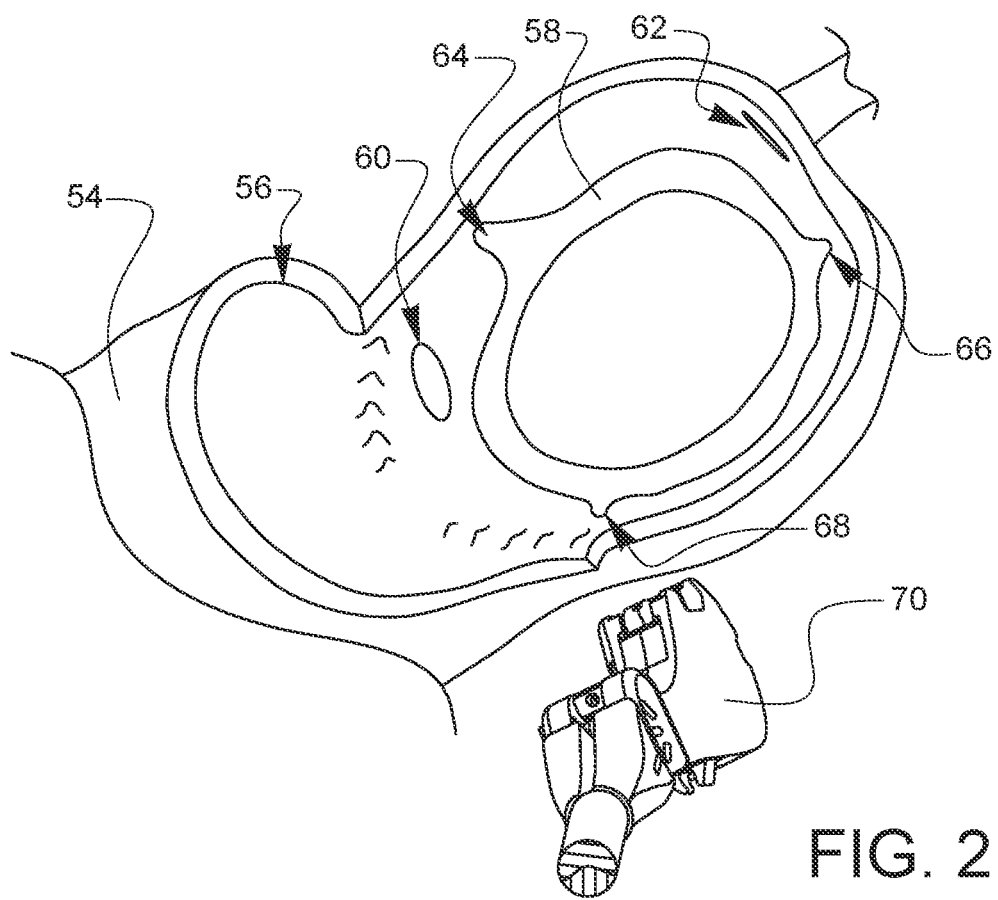
Figure 2C:
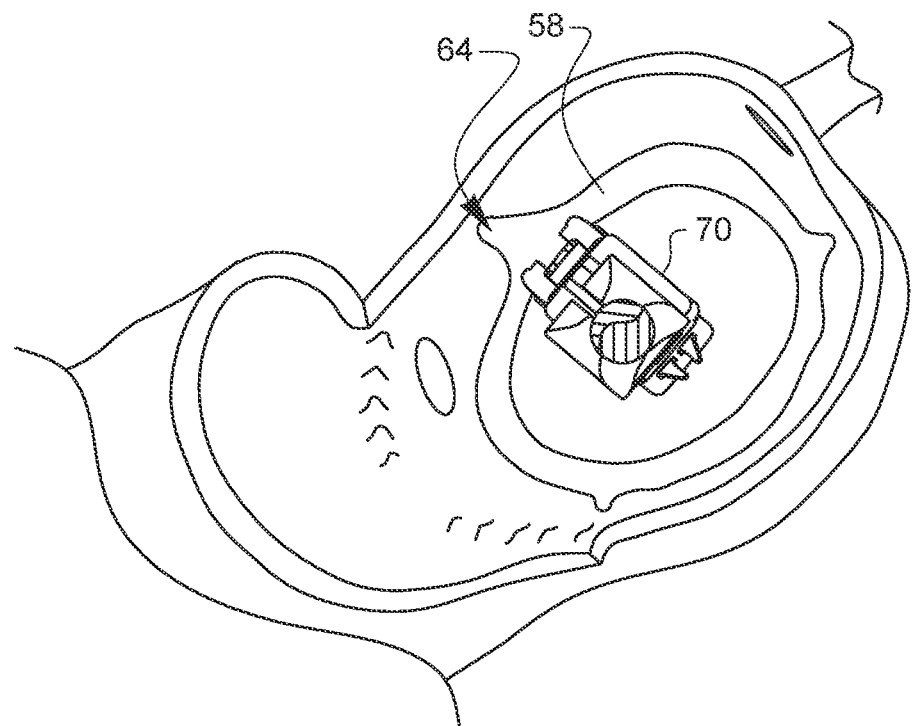
Figure 2D:
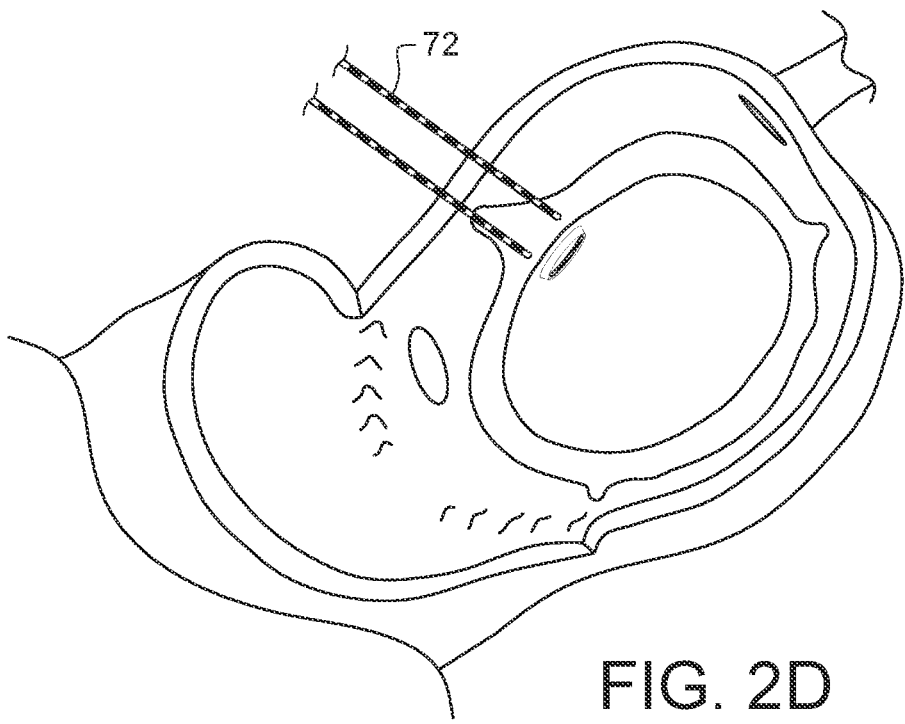
Figure 2E:
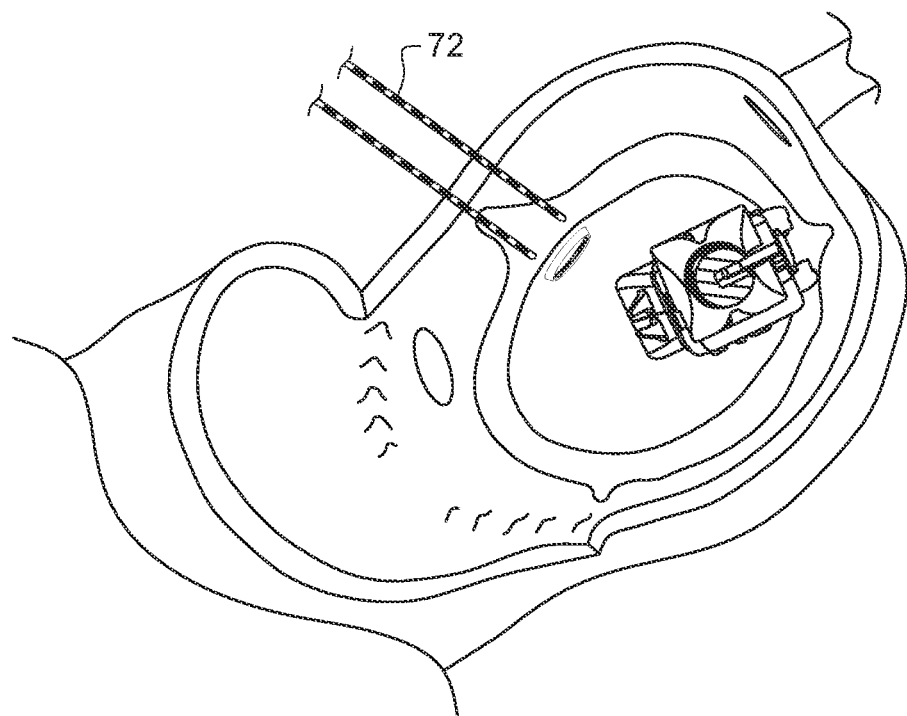
Figure 2F:
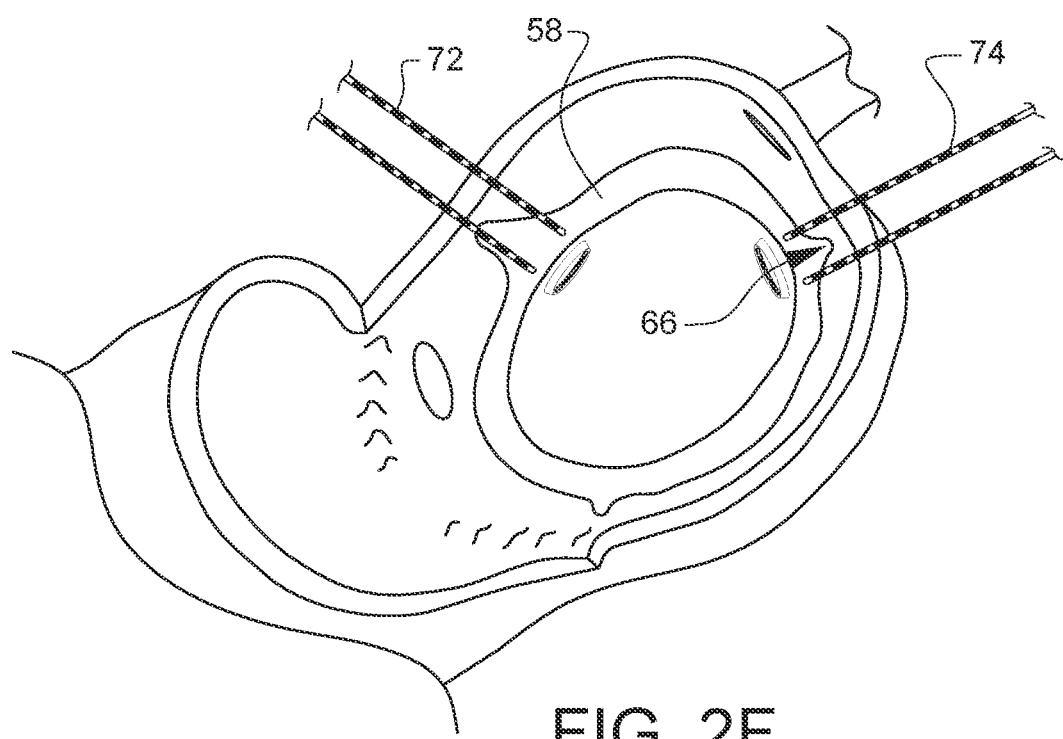
Figure 2G:
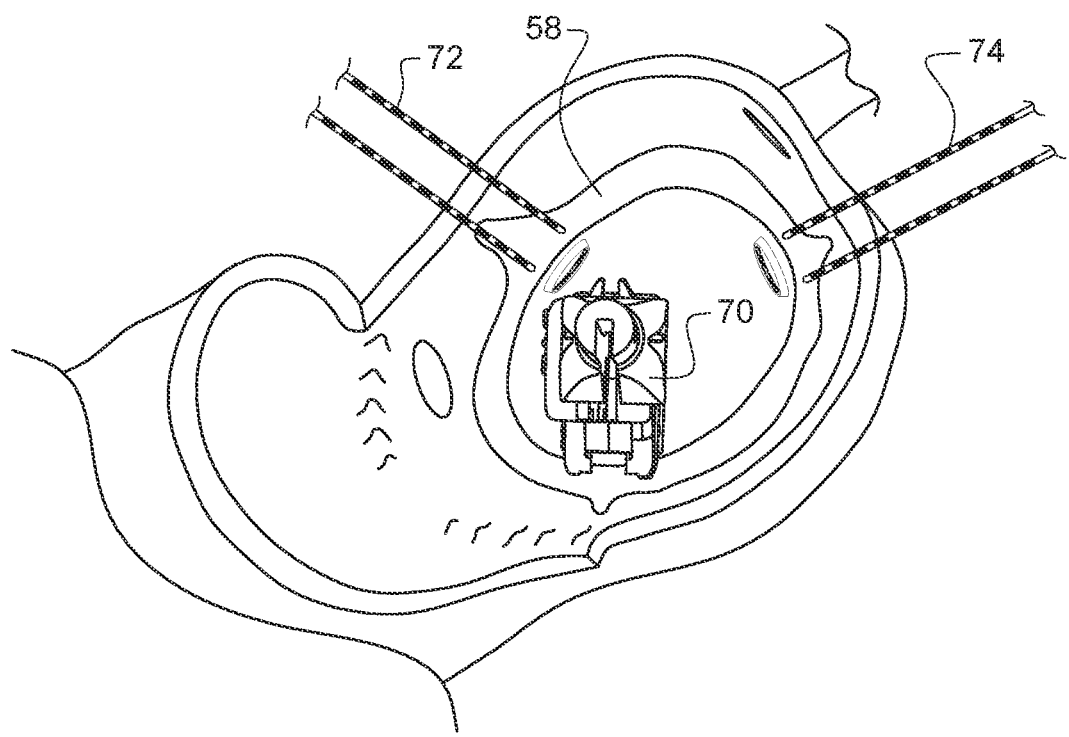
Figure 2H:
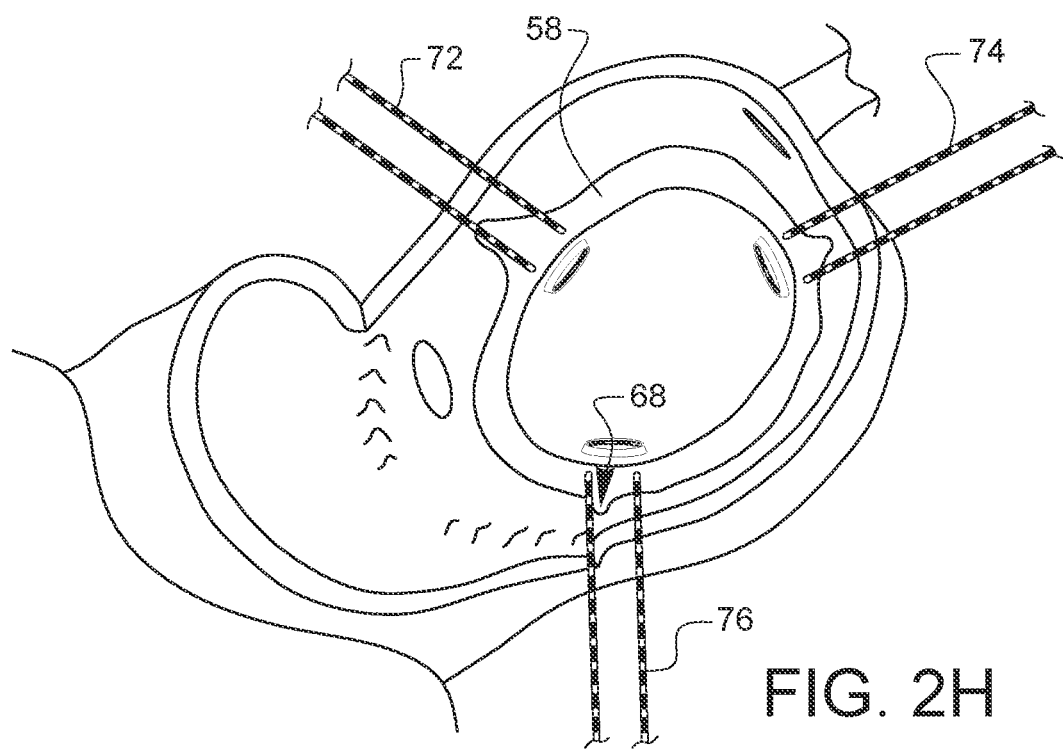
Figure 2I:
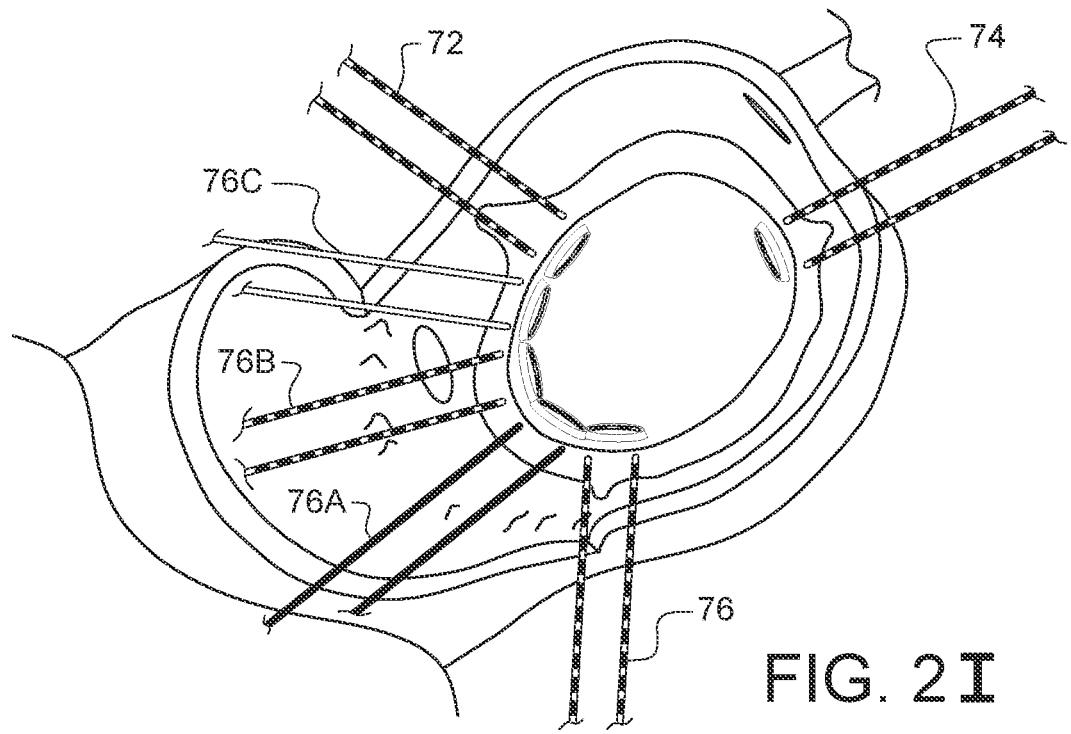
Figure 2J:
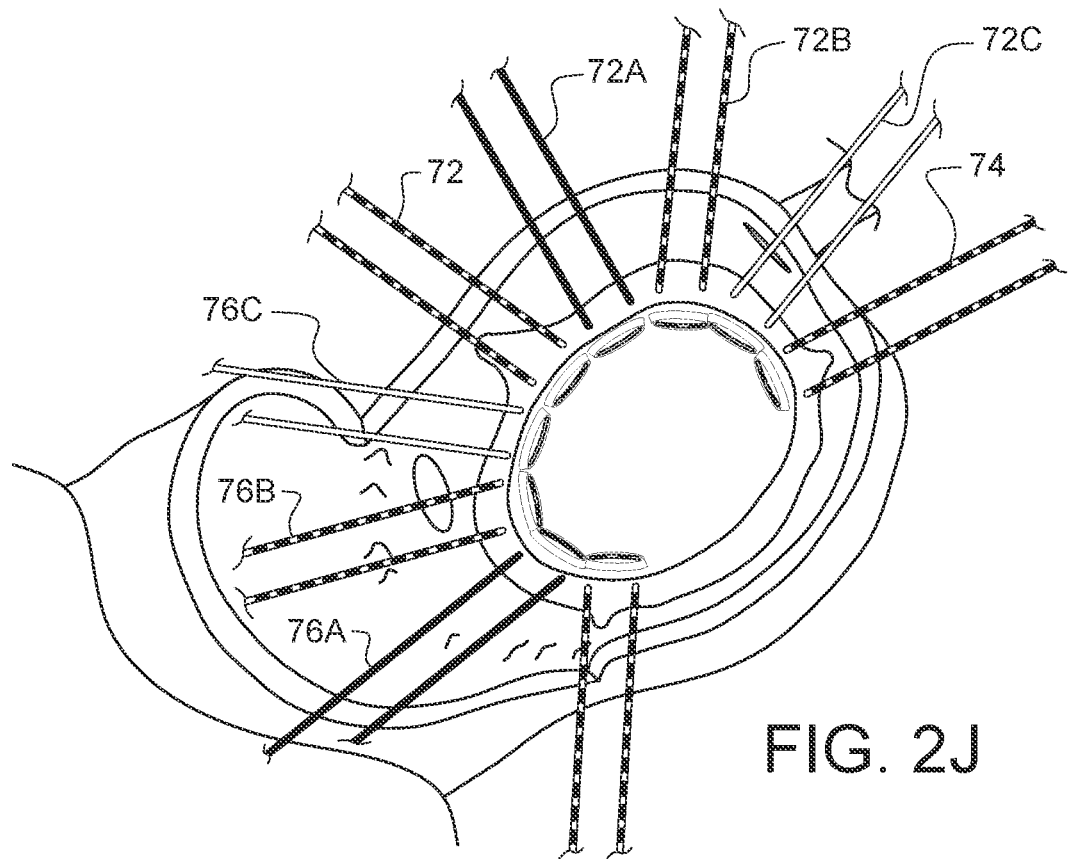
Figure 2K:
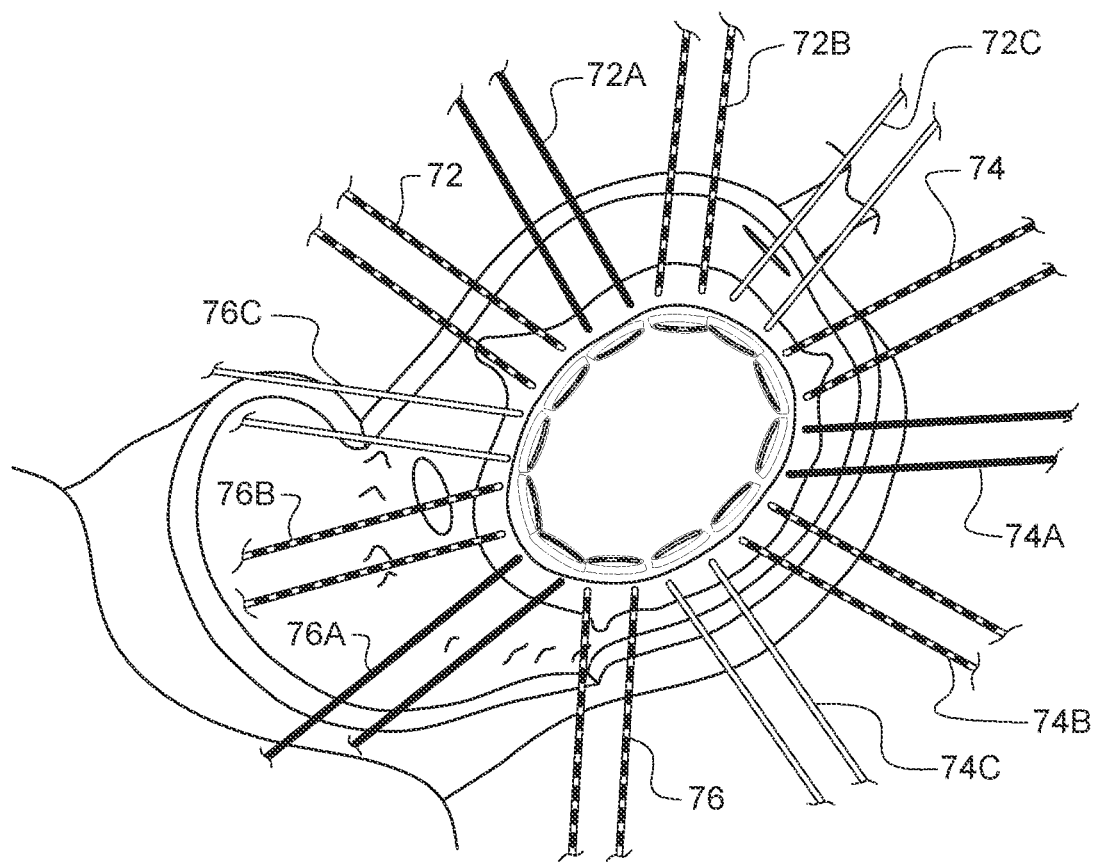

In FIGS. 2B and 2C, a minimally invasive suturing device 70 is brought into contact with the aortic root 58 at the left-right commissure 64, and a pledgeted mattress suture 72 is stitched into the aortic root 58 as shown in FIG. 2D. Other types of minimally invasive suturing devices could be used, or the stitch could be placed by hand. As illustrated in FIGS. 2E and 2F, a pledgeted mattress suture 74 is placed in the aortic root 58 at the right-non-coronary commissure 66. As illustrated in FIGS. 2G and 2H, a pledgeted mattress suture 76 is placed in the aortic root 58 at the non-coronary-left commissure 68. A variety of methods are possible for filling in the remaining stitches between these commissural stitches, but generally, surgeons can fit about three additional stitches—72A, 72B, 72C, 74A, 74B, 74C, 76A, 76B, and 76C—between each of the commissures as illustrated in FIGS. 2I-2K. As shown in FIG. 2K, there are twelve sutures and twenty-four suture ends just from the stitches placed in the aortic root alone. Not only do the sutures need to remain untangled, but suture ends from the same suture need to be kept together as a pair for later steps in the operation. Add in stay sutures and the fact that these sutures pass out of narrowly accessible areas where surgical instruments must move and it is easier to appreciate why tools for suture management are very important.

Figure 3A:
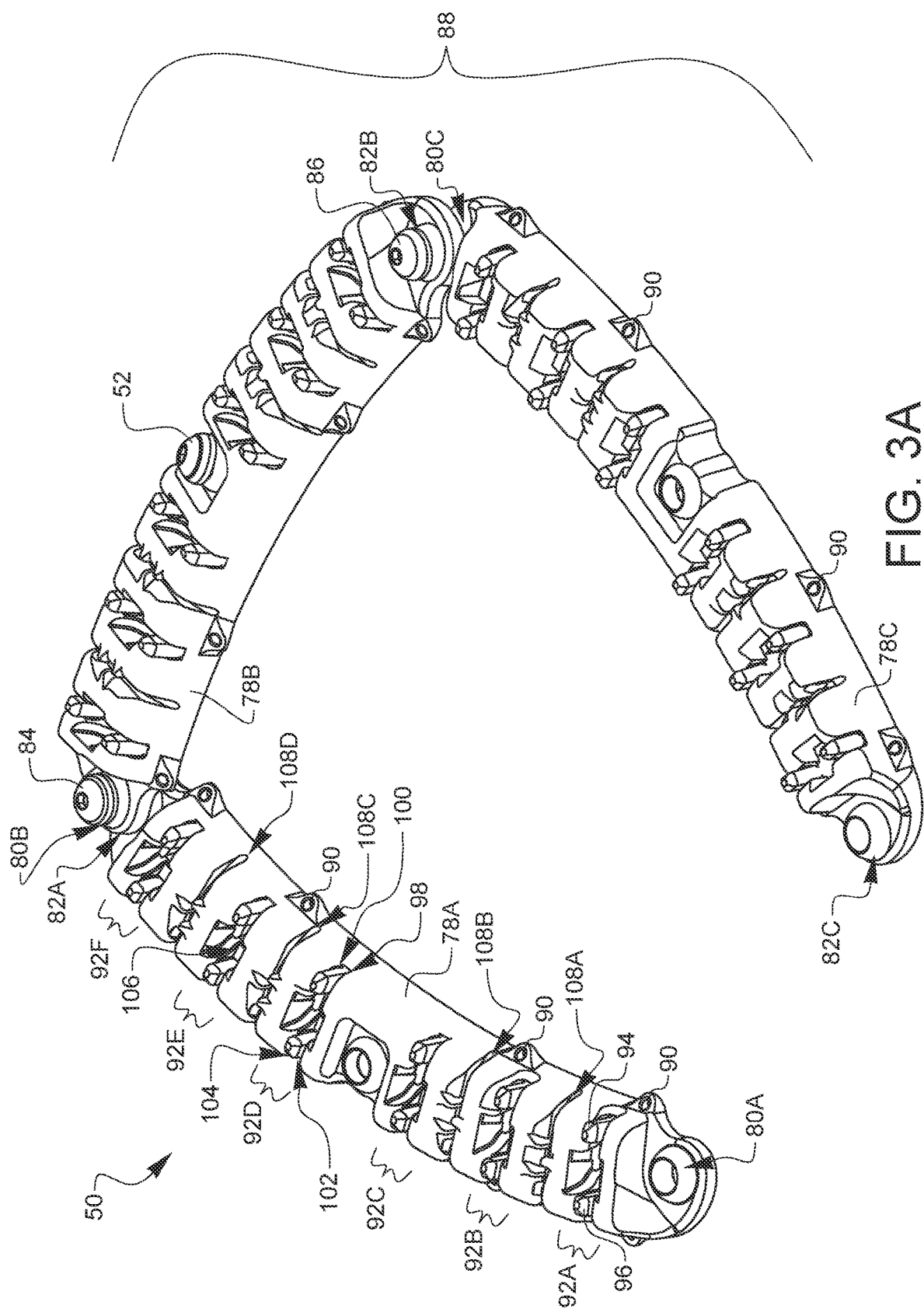
FIG. 3A is a perspective view of an embodiment of an apparatus for suture management.

FIG. 3A is a perspective view of an embodiment of an apparatus for suture management. The apparatus for suture management 50 has one or more racks 78A, 78B, 78C. The racks 78A, 78B, 78C define several connection points 80A, 82A on rack 78A. Similarly, rack 78B has rack connection points 80B, 82B, and rack 78C has rack connection points 80C, 82C. One rack may be connected to another rack by aligning two connection points and coupling them together with a rack attachment device. In the embodiment of FIG. 3A, rack 78A is coupled to rack 78B by a bolt 84 and nut (not visible in this view). The bolt 84 and its corresponding nut are an example of a rack attachment device. The bolt 84 passes through the aligned rack connection points 80B and 82A and then threads into the nut (not visible) which is then tightened when the racks are aligned relative to each other as desired. Similarly, rack 78B is coupled to rack 78C by a bolt 86 and nut (not visible in this view). The bolt 86 and its corresponding nut are another example of a rack attachment device. The bolt 84 passes through the aligned rack connection points 82B and 80C and then threads into the nut (not visible) which is then tightened when the racks are aligned relative to each other as desired. The racks may come pre-assembled as shown in FIG. 3A, or the racks may be separated for end-user assembly. The rack attachment devices, here bolts 84, 86 and their corresponding nuts (not visible in this view) may be configured to be tightened or loosened by a key from a surgical retractor or any other tool, as desired, depending on the embodiment.

When multiple racks 78A, 78B, 78C are joined together, we refer to this as a ring 88, even though the joined racks may not form a continuous loop. As noted earlier, one of the racks 78B may be provided with an attachment feature 52 for coupling to a retractor or other surgical support or surgical equipment holder.

One or more racks 78A, 78B, 78C or the ring 88 may alternately be positioned around an incision site by using a clamp such as, but not limited to a towel clamp. Each rack 78A, 78B, 78C has multiple clamp receivers or anchor points 90 which may be used in conjunction with a towel clamp in order to clamp the rack or ring to a surgical drape or towel. Such a towel clamp could attach to the ring 88 at one or more anchor points 90. Alternatively, other attaching clamps or fastening methods, such as sewn sutures may be used in one or more anchor points 90 to hold or position the ring 88 around an incision site.

Each rack 78A, 78B, 78C is similar in its features for suture management, so for convenience, only the features of a single rack will be discussed. It should be understood, however, that the additional racks in a ring are similar. In this embodiment, the rack 78A has a plurality of cassette locations 92A, 92B, 92C, 92D, 92E, and 92F. Other embodiments may have more or fewer cassette locations. Each of the cassette locations 92A-92F has an inner suture holder 94 and an outer suture holder 96, each preferably, but not necessarily, made from a flexible material. As will be discussed later, each inner and outer suture holder 94, 96 for a given cassette position 92A-92F are part of a soft insert which is pushed into the bottom of the rack 78A.

The inside suture holder 94 in each cassette location 92A-92F creates an inside counter-clockwise (CCW) holding slot 98 and an inside clockwise (CW) holding slot 100 on the CCW and CW sides of each inside suture holder 94, respectively. Similarly, the outside suture holder 96 in each cassette location creates an outside CCW holding slot 102 and an outside CW holding slot 104 on the CCW and CW sides of the outside suture holder 96. For each cassette location 92A-92F, the inside and outside CCW holding slots 98, 102 are designed to receive and hold a first segment of suture (not shown) from a SEW-EASY™ Cassette (not shown in this view, but is available from LSI Solutions, Inc. at www.lsisolutions.com). Likewise, the corresponding inside and outside CW holding slots 100, 104 are designed to receive and hold a second segment of suture from the SEW-EASY™ Cassette. Each cassette location 92A-92F also has a cassette receiver 106 which is sized to hold and easily release the tip of a SEW-EASY™ Cassette after the suture segments from that Cassette have been inserted into the holding slots for that cassette location. In some embodiments, the cassette receiver 106 may be defined by the rack, or defined by a soft insert, which will be described later.

The rack 78A also has a plurality of suture grooves 108A, 108B, 108C, 108D. As will be seen in one of the following views, the suture grooves 108A-108D have their own corresponding soft inserts which are installed in the bottom of the rack and may be used to help capture suture. The suture grooves 108A-108D are available to hold and organize stay sutures. The suture grooves 108A-108D also feature a tortuous path shape which is convenient for holding suture tubes which surgeons often use as part of a tourniquet.

Figure 3B:
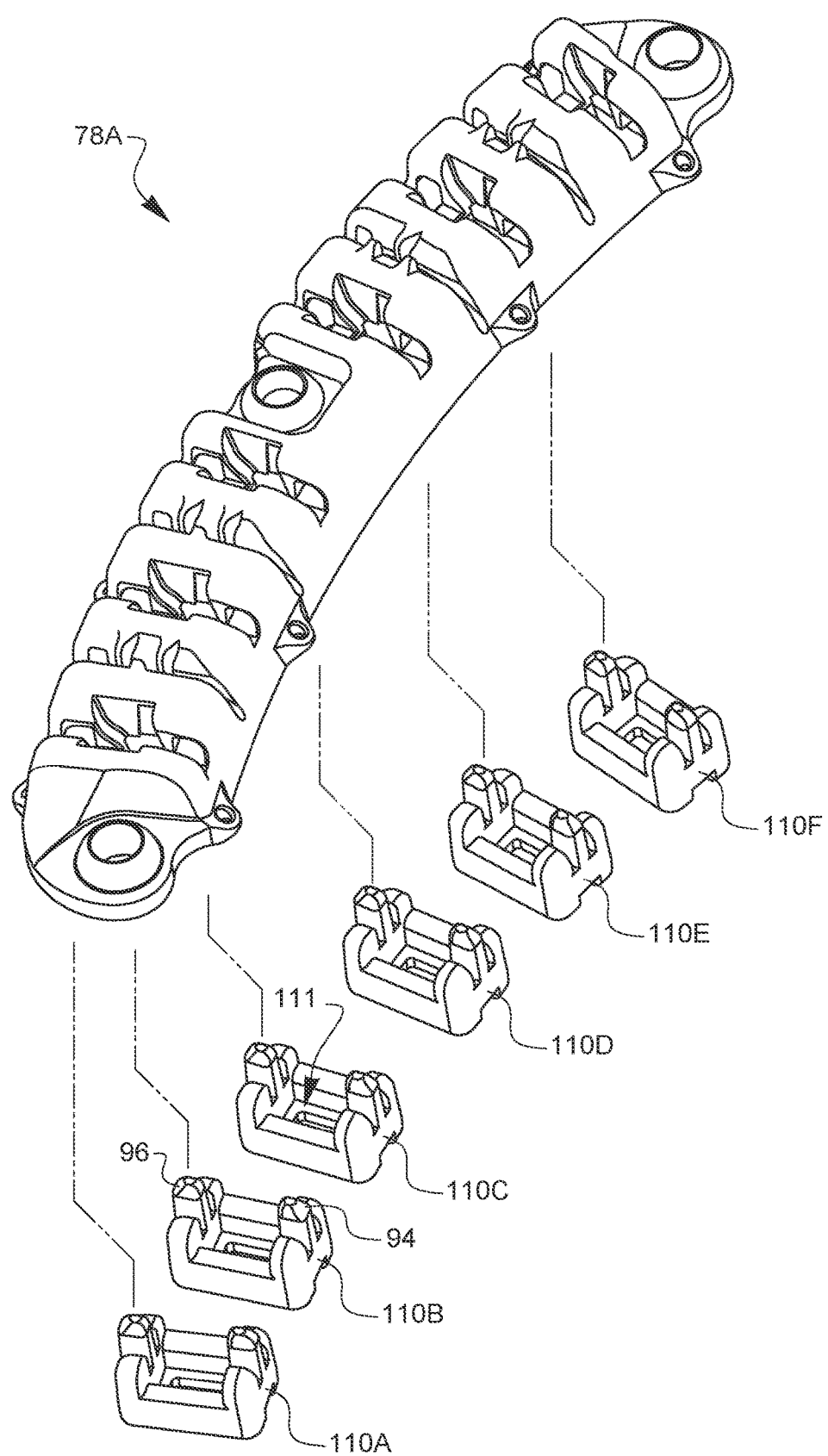
FIG. 3B is a top-right perspective view of an assembly step of the apparatus for suture management of FIG. 3A.

FIG. 3B is a top-right perspective view of an assembly step of the apparatus for suture management of FIG. 3A. FIG. 3B illustrates a rack 78A which shows soft inserts 110A, 110B, 110C, 110D, 110E, and 110F exploded from the rack 78A in order to better show the soft inserts for cassette positions 92A-92F, respectively. Each soft insert 110A-110F has the inside suture holder 94 and the outside suture holder 96 as discussed above. Each soft insert 110A-110F also defines a central cavity 111 which lines a corresponding cassette receiver 106 to help provide friction which holds a SEW-EASY™ cassette in place when inserted therein. In the example of FIG. 3A, each of the soft inserts is a similar color. In the example of FIG. 3B, the soft insert 110A is a first color, while the remaining soft inserts 110B-110F are a second color. This may be useful with the suture management. For example, when three racks are combined into a ring, there would be three cassette locations (one in each rack) which would have a first color. The remaining positions would be a second color. The three cassette locations of the first color could be used for the stitches placed in the commissures of the aortic root. The available positions of second color between the commissure locations could then be filled in an order corresponding to additional stitches which are placed in the aortic root. Depending on the surgical procedure, soft inserts of multiple colors could be utilized to correspond to specific steps in a procedure to facilitate suture management and easy visual identification by the user or operator. The soft inserts described herein may be made from a resilient material or flexible material such as an appropriate polymer such as a polyurethane, silicone or other flexible polymer known to those skilled in the art. Alternatively, the soft inserts may define a textured or otherwise specifically shaped surface to provide increased friction or holding force for releasably holding sutures, modular cassettes, or other surgical items in place.

Figure 3C:
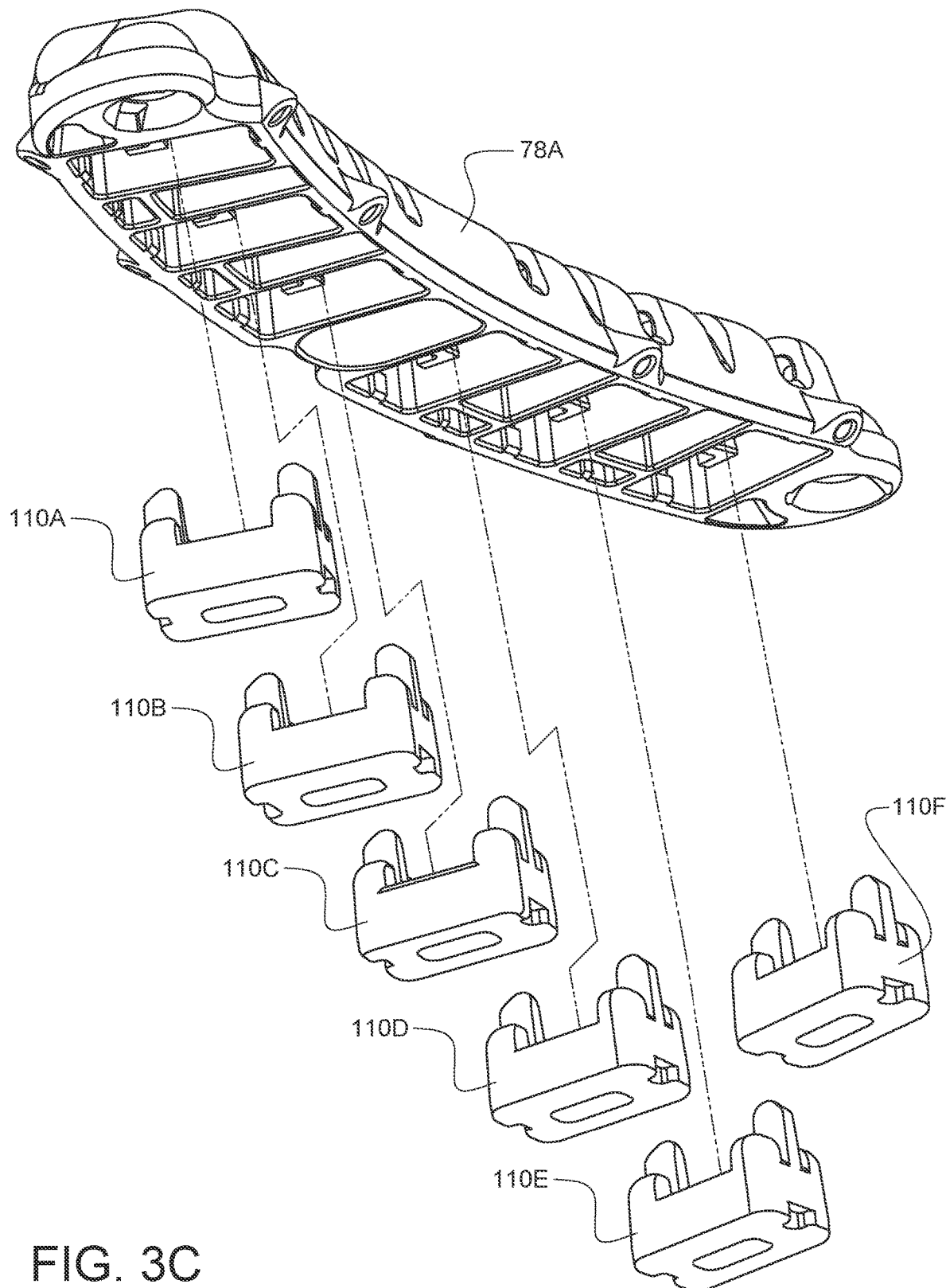
FIG. 3C is a bottom-right perspective view of the assembly step of FIG. 3B of the apparatus for suture management of FIG. 3A.
Figure 3D:
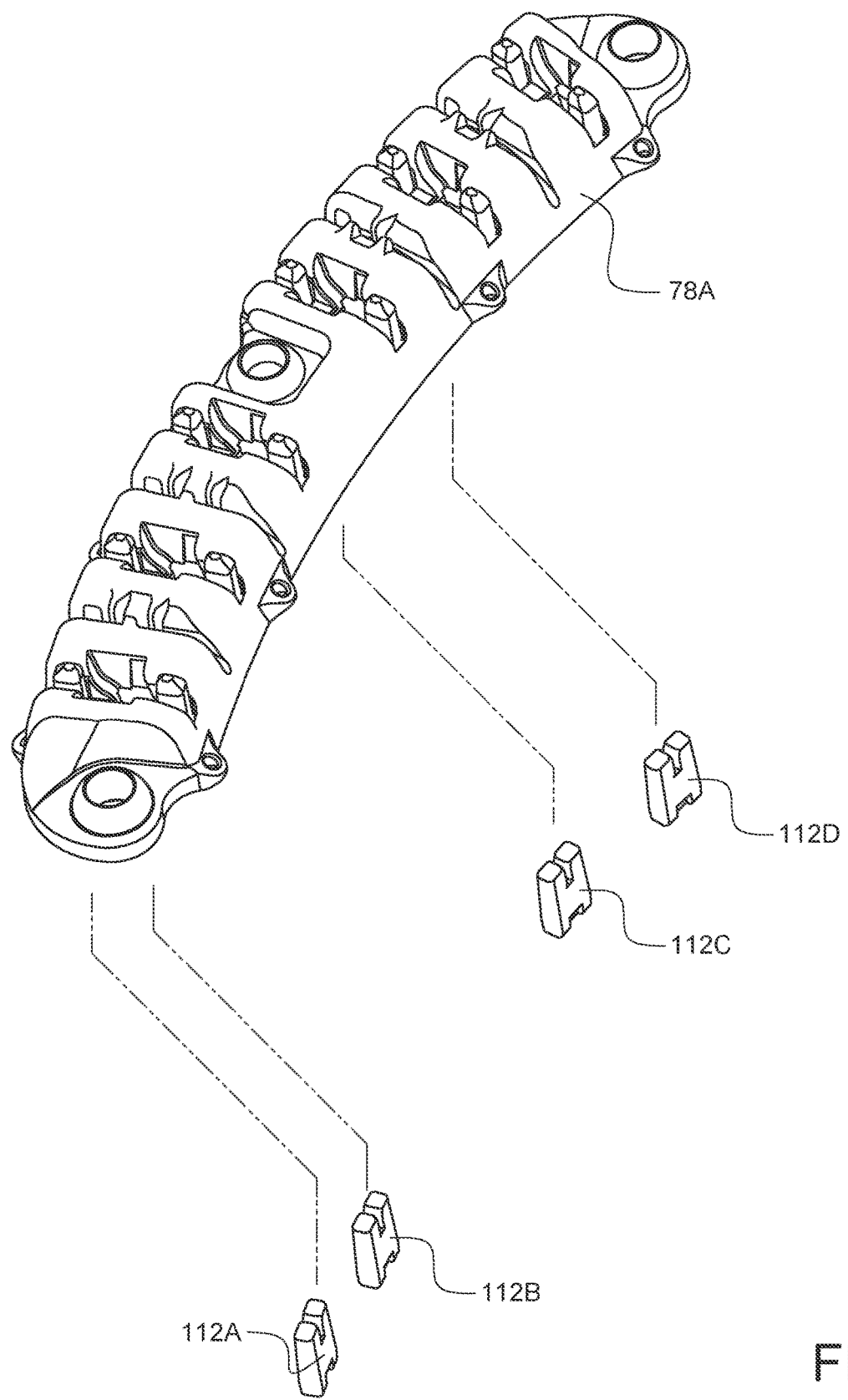
FIG. 3D is a top-right perspective view of another assembly step of the apparatus for suture management of FIG. 3A.
Figure 3E:
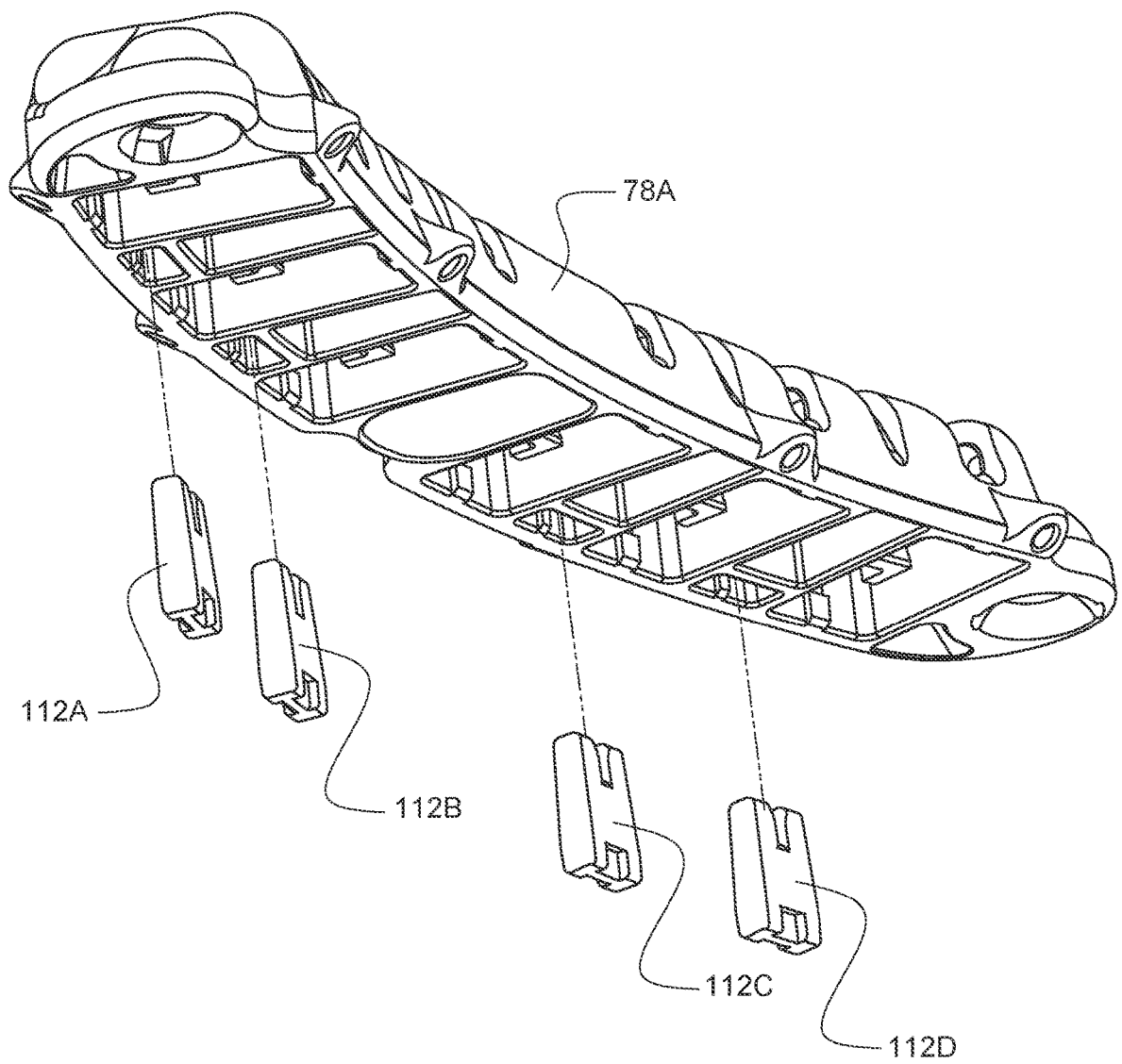
FIG. 3E is a bottom-right perspective view of the assembly step of FIG. 3D of the apparatus for suture management of FIG. 3A.

FIG. 3C is a bottom-right perspective view of the assembly step of FIG. 3B of the apparatus for suture management of FIG. 3A. FIG. 3C shows more clearly where the soft inserts 110A-110F will be placed in the rack 78A. FIGS. 3D and 3E are top-right and bottom-right perspective exploded views, respectively, of a separate set of soft inserts 112A, 112B, 112C, and 112D which are coupled into the rack 78A in alignment with the suture grooves 108A, 108B, 108C, 108D discussed above.

Figure 3F:
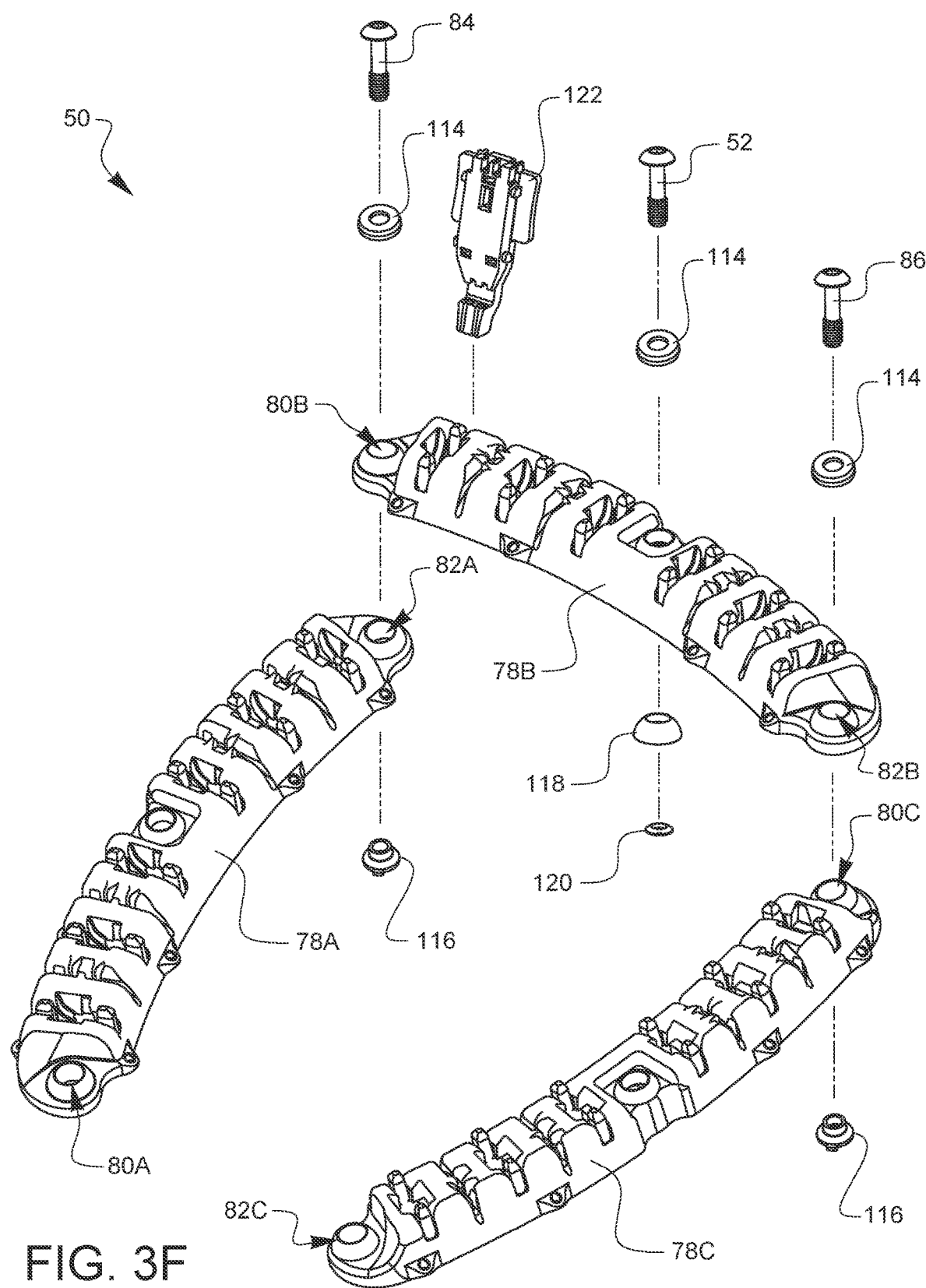
FIG. 3F is a top-right perspective view of an exploded assembly step of the apparatus for suture management of FIG. 3A.

FIG. 3F is a top-right perspective view of an exploded assembly step of the apparatus for suture management of FIG. 3A. FIG. 3F illustrates the bolts 84, 86, nuts 116, and washers 114 for assembly of the respective racks 78A, 78B, and 78C which were not visible in previous views, as well as the washer 114, a pivot dome 118, and a retaining clip 120 for mounting the attachment feature 52 to rack 78B. A SEW-EASY™ cassette 122 is also pictured in alignment with one of the cassette receivers, but the SEW-EASY™ cassette 122 does not form a part of the apparatus for suture management 50.

Figure 4A:
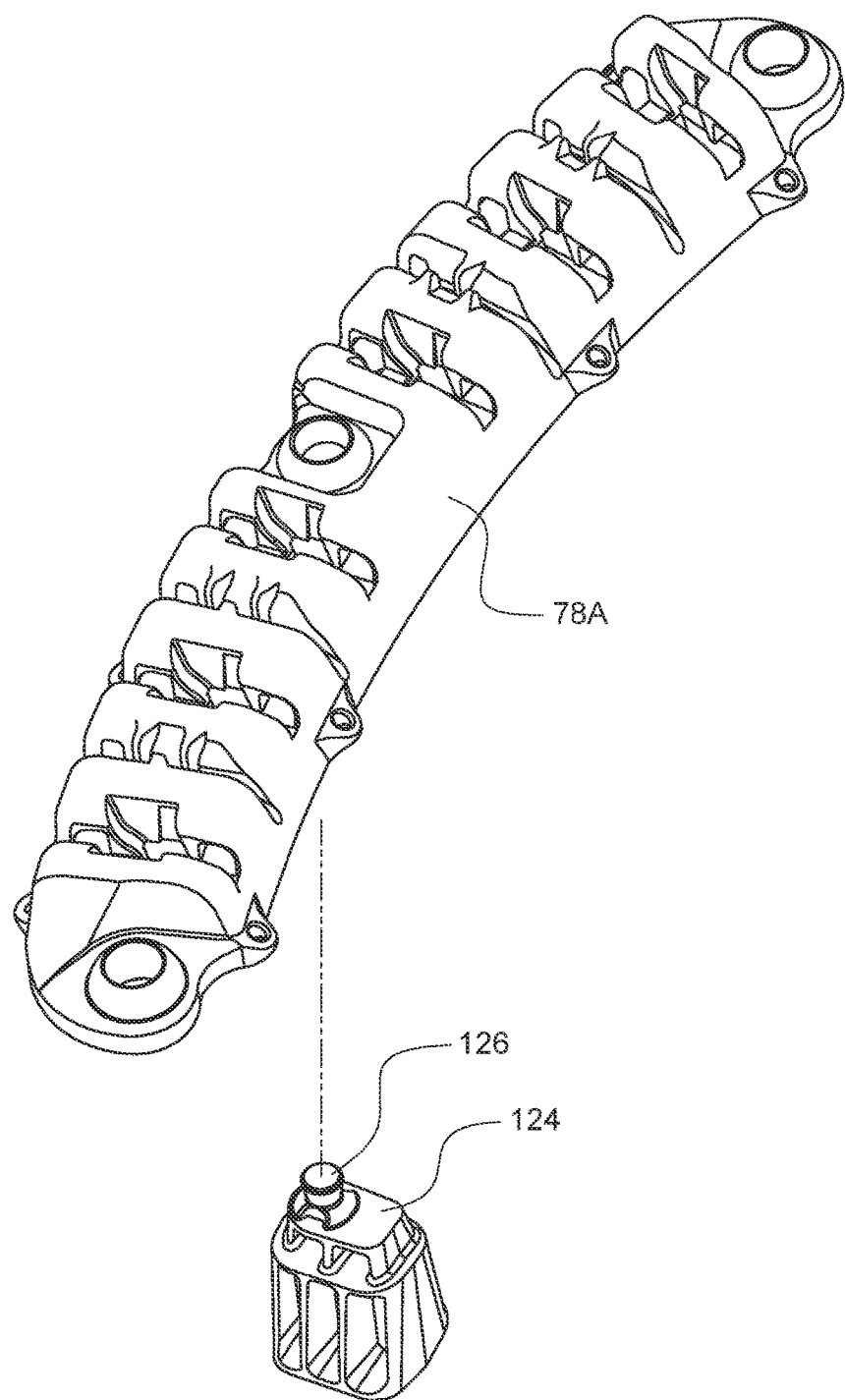
FIG. 4A is a top-right perspective view of an additional assembly step of the apparatus for suture management of FIG. 3A.
Figure 4B:
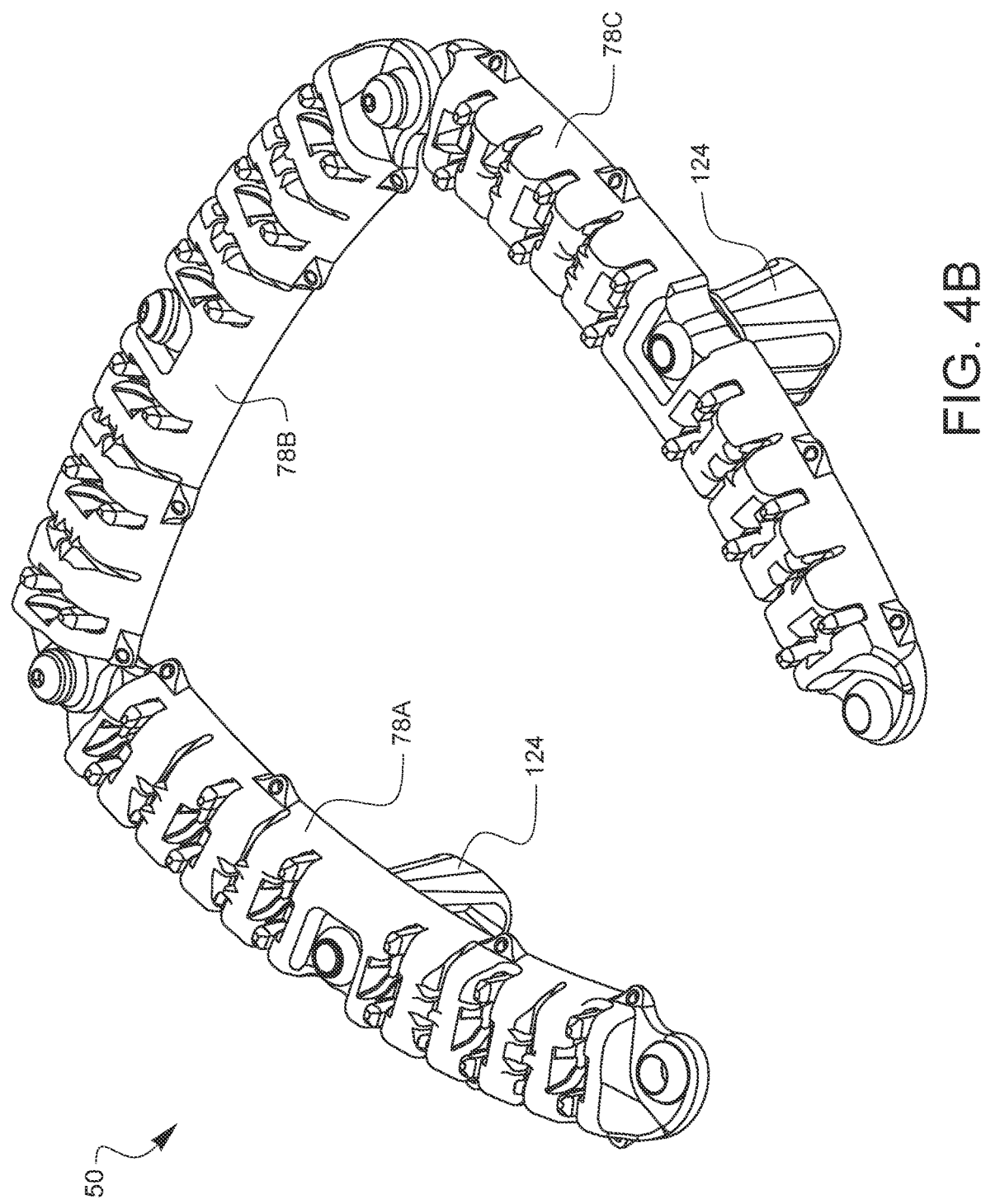
FIG. 4B is a top-right perspective view of the fully assembled apparatus for suture management of FIG. 3A.

FIG. 4A is a top-right perspective view of an additional assembly step of the apparatus for suture management of FIG. 3A. FIG. 4A shows the addition of a stabilizing foot 124 to rack 78A. The foot 124 is configured to stabilize the apparatus for suture management 50 when in use, for example against a patient's chest. The stabilizing foot 124 defines an attachment post 126 which is configured to be inserted into the underside of the rack 78A in assembly. FIG. 4B is a top-right perspective view of the fully assembled apparatus for suture management of FIG. 3A. FIG. 4B illustrates the fully assembled apparatus for suture management 50.

Various advantages of an apparatus for suture management have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An apparatus for suture management, the apparatus comprising:
   at least two rack portions that each extends from a first end to a second end along a rack axis, wherein a plurality of slots are formed in each of the at least two rack portions, and each of the plurality of slots extends from a first end offset from a first lateral edge of each of the at least two rack portions to a second end offset from a second lateral edge of each of the at least two rack portions; and
   at least one insert coupled to each of the at least two rack portions, the at least one insert having a base portion and at least one projection that extends from the base portion, wherein the base portion is disposed within a cavity formed by one or more underside surfaces of each of the at least two rack portions, wherein the at least one projection extends through a corresponding one of the plurality of slots such that an end portion of the at least one projection is offset from an outer surface of each of the at least two rack portions,
   wherein a first clockwise holding slot is defined between a first surface of the at least one projection and a first edge defining the corresponding one of the plurality of slots, wherein the first clockwise holding slot is configured to receive a first suture segment, wherein a first counterclockwise holding slot is defined between a second surface of the at least one projection and a second edge defining the corresponding one of the plurality of slots, wherein the first counterclockwise holding slot is configured to receive a second suture segment, wherein a receiving depression is formed in a portion of the base, the receiving depression being aligned with a receiving portion of the corresponding one of the plurality of slots that is disposed between the first end and the second end of the corresponding one of the plurality of slots, wherein the receiving depression is configured to removably receive a tip portion of a cassette, and wherein the at least two rack portions includes a first rack portion and a second rack portion, wherein the second end of the first rack portion is releasably coupled to the first end of the first rack portion.

2. The apparatus for suture management of claim 1, wherein the at least one projection of the at least one insert includes a first projection and a second projection, wherein the first projection is disposed adjacent to the first end of the corresponding slot and the second projection is disposed adjacent to the second end of the corresponding slot.

3. The apparatus for suture management of claim 1, wherein the receiving portion of the corresponding one of the plurality of slots is defined by at least one edges that extends in a direction substantially transverse to the rack axis to at least partially define a transverse notch that extends through the corresponding one of the plurality of slots.

4. The apparatus for suture management of claim 1, wherein the at least one insert includes a plurality of inserts, with each of the plurality of inserts corresponds to each of the plurality of slots formed in the first rack portion.

5. The apparatus for suture management of claim 4, wherein each base portion of the plurality of inserts is disposed within a corresponding one of a plurality of cavities formed by the one or more underside surfaces of each of the at least two rack portions.

6. The apparatus for suture management of claim 1, wherein the wherein the second end of the first rack portion is pivotably coupled to the first end of the first rack portion.

7. The apparatus for suture management of claim 1, wherein the at least two rack portions includes a third rack portion that extends from a first end to a second end, wherein the second end of the second rack portion is releasably coupled to the second end of the third rack portion.

8. The apparatus for suture management of claim 7, wherein the wherein the second end of the first rack portion is pivotably coupled to the first end of the first rack portion and the second end of the second rack portion is pivotably coupled to the second end of the third rack portion.

9. The apparatus for suture management of claim 1, wherein the rack axis of each of the at least two rack portions is non-linear.

10. The apparatus for suture management of claim 1, wherein the rack axis has a cambered shape.

11. The apparatus for suture management of claim 1, wherein the at least one insert coupled to each of the at least two rack portions comprises a resilient material.

12. The apparatus for suture management of claim 11, wherein the at least one insert coupled to each of the at least two rack portions is made from a polyurethane material or a silicone material.

13. The apparatus for suture management of claim 1, wherein the at least one insert coupled to each of the at least two rack portions includes a first insert coupled to a first rack portion and a second insert coupled to a second rack portion, and wherein the first insert is a first color and the second insert is a second color.

14. The apparatus for suture management of claim 1, wherein at least one of the at least two rack portions includes an attachment feature configured to secure the at least one of the at least two rack portions to a surgical instrument.

15. The apparatus for suture management of claim 1, wherein each of the plurality of slots extends from the first end to the second end along a slot axis that is normal to the rack axis.

16. An apparatus for suture management, the apparatus comprising:

a first rack portion that extends from a first end to a second end along a rack axis, wherein a plurality of slots are formed in the first rack portion, and each of the plurality of slots extends from a first end offset from a first lateral edge of the first rack portion to a second end offset from a second lateral edge of the first rack portion; and a plurality of inserts coupled to the first rack portion, each of the plurality of inserts having a base portion and at least one projection that extends from the base portion, wherein the base portion is disposed within a corresponding cavity formed by one or more underside surfaces of the first rack portion, wherein the at least one projection extends through a corresponding one of the plurality of slots such that an end portion of the at least one projection is offset from an outer surface of the first rack portion, wherein a plurality of first clockwise holding slots are defined between a first surface of the at least one projection of each of the plurality of inserts and a first edge defining the corresponding one of the plurality of slots, wherein each of the plurality of first clockwise holding slots is configured to receive a first suture segment, wherein a plurality of first counterclockwise holding slots are defined between a second surface of the at least one projection of each of the plurality of inserts and a second edge defining the corresponding one of the plurality of slots, wherein each of the plurality of first counterclockwise holding slots is configured to receive a second suture segment, wherein a receiving depressions is formed in a portion of the base of each of the plurality of inserts, the receiving depression being aligned with a receiving portion of the corresponding one of the plurality of slots that is disposed between the first end and the second end of the corresponding one of the plurality of slots, wherein the receiving depression is configured to removably receive a tip portion of a cassette, and wherein one or both of the first end or the second end of the first rack portion is adapted to be pivotably coupled to an end of a second rack portion.

17. The apparatus for suture management of claim 16, wherein each of the plurality of inserts comprises a resilient material.

18. The apparatus for suture management of claim 16, wherein each of the plurality of slots extends from the first end to the second end along a slot axis that is normal to the rack axis.

19. The apparatus for suture management of claim 16, wherein the at least one projection of each of the plurality of inserts includes a first projection and a second projection, wherein the first projection is disposed adjacent to the first end of the corresponding slot and the second projection is disposed adjacent to the second end of the corresponding slot.

20. The apparatus for suture management of claim 16, wherein the rack axis has a cambered shape.

* * * * *